US00PP30532P3

(12) United States Plant Patent
Hansen

(10) Patent No.: US PP30,532 P3
(45) Date of Patent: May 21, 2019

(54) **X *HEUCHERELLA* PLANT NAMED 'EYE SPY'**

(50) Latin Name: **X *Heucherella* (*Heuchera* x *Tiarella*)**
Varietal Denomination: Eye Spy

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 25 days.

(21) Appl. No.: 15/731,995

(22) Filed: Sep. 5, 2017

(65) Prior Publication Data

US 2019/0075704 P1 Mar. 7, 2019

(51) Int. Cl.
*A01H 5/02* (2018.01)
*A01H 6/80* (2018.01)

(52) U.S. Cl.
USPC ..... Plt./441
CPC ..... *A01H 6/80* (2018.05)

(58) Field of Classification Search
USPC ..... Plt./441
See application file for complete search history.

*Primary Examiner* — Anne Marie Grunberg

(57) ABSTRACT

The new hybrid X *Heucherella* plant named 'Eye Spy' with moderately cleft palmately lobed foliage having acute apices and variable coloration starting in the spring as amber yellow-colored with dark rose centers, transitioning to bright chartreuse green with slight silver overlay and burgundy surrounding the veins. 'Eye Spy' produces a pink flower effect from fine white petals, pink calyces and deep rose buds beginning in late spring. Habit is low mounded and winter-hardy plants are able to withstand more heat and sun than typical X *Heucherella* cultivars.

1 Drawing Sheet

Botanical denomination: X *Heucherella* (*Heuchera* x *Tiarella*).

Cultivar designation: 'Eye Spy'.

BACKGROUND OF THE INVENTION

The present invention relates to a new and distinct intergeneric hybrid between Coral Bells and Foam Flower, both in the Saxifragaceae family and given the cultivar name of 'Eye Spy' with the combined generic epithet X *Heucherella*. X *Heucherella* 'Eye Spy' resulted from an intentional cross between the unreleased proprietary *Heuchera* hybrid known by the breeder code 12-62-03 (not patented) as the female or seed parent and the unreleased proprietary *Tiarella* hybrid known by the breeder code 11-14-08 as the male or pollen parent. The new plant was hybridized by Hans A. Hansen at a wholesale perennial nursery in Zeeland, Mich., USA on Jan. 31, 2013 and seeds from the cross harvested in the spring of 2013. The new plant passed the original evaluation in summer 2013 and was given the breeder code of 13-99-9 in the spring of 2014 through the subsequent years of further evaluations. The new plant was selected from among many other crosses and X *Heucherella* seedlings growing at the same nursery in Zeeland, Mich. which met the rigorous criteria of excellent foliage and habit established as breeding goals. X *Heucherella* 'Eye Spy' has been asexually propagated since 2014 by division of the rhizome at a nursery in Zeeland, Mich. and also by careful shoot tissue culture propagation. The resultant asexually propagated plants have remained stable and exhibit the same characteristics as the original plant.

No plants of X *Heucherella* 'Eye Spy' have been disclosed or sold, under this or any name, in this country or anywhere in the world, prior to the filing of this application, with the exception of that which may have been disclosed within one year of the filing of this application and was either derived directly or indirectly from the inventor.

BRIEF SUMMARY OF THE INVENTION

X *Heucherella* 'Eye Spy' differs from its parents as well as all other X *Heucherella* known to the applicant. Compared with the female parent with coral red flowers with deep rose buds, the new plant has light pink flowers with light rose buds. The foliage of the female parent is less dissected with rounded apices, has a general burgundy color with silver overlay. The male parent has a chartreuse to light green leaf margin and the flowers are near white compared with the new plant. The most similar cultivars include: X *Heucherella* 'Alabama Sunrise' U.S. Plant Pat. No. 19,611 and 'Stoplight' U.S. Plant Pat. No. 16,835.

Compared with the new plant, 'Stoplight' has shallower cleft foliage with more rounded lobes and the flowers and buds are not as pink and rose-colored respectively. Compared with the new plant, 'Alabama Sunrise' has more deeply cleft foliage with thinner burgundy coloration surrounding the veins and the flowers and buds are white The new plant differs from all *Heuchera*, X *Heucherella* and *Tiarella* known to the inventor in the following combined traits:

1. The foliage color of X *Heucherella* 'Eye Spy' is variable with the seasons starting in the spring as an amber yellow-colored with dark rose centers.
2. Leaves transition to bright chartreuse green with slight silver overlay and burgundy surrounding the veins.
3. The leaf blade shape is moderately cleft with sharp lobes tips.
4. The flower petals are near-white with pink calyces and deep rose buds, tightly arranged on panicles just over the foliage in late spring.

5. Habit is low mounded with multiple tightly clustered shoots emerging at the base all season.
6. The plant is robust, seedless, compact and is more heat and sun tolerant than typical X *Heucherella*.

BRIEF DESCRIPTION OF THE DRAWINGS

The photographs of the new plant demonstrate the overall appearance of 'Eye Spy' including the unique traits. The plant in the photograph is of a two-year old plant grown in a double-poly coated greenhouse without further shading, with supplemental fertilizer and water as needed at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
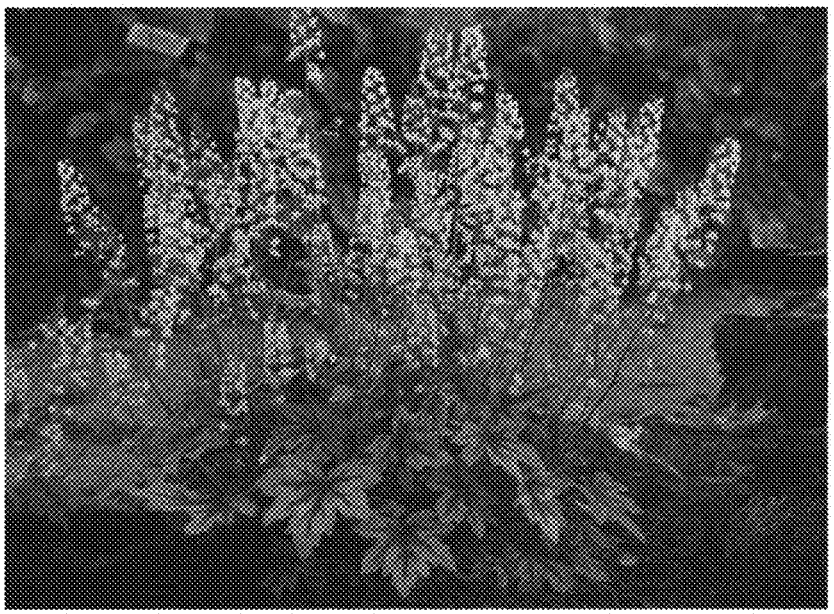
FIG. 1 shows a two-year-old plant in a shaded trial garden in Zeeland, Mich. in peak spring flowering.
Figure 2:
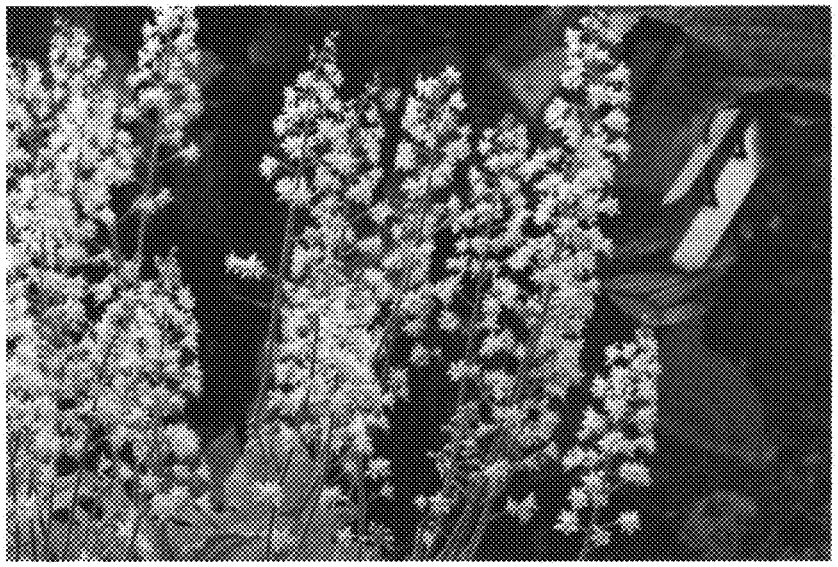
FIG. 2 shows a close-up of the flowers and buds.

The following description is based on two-year-old and three-year-old plants growing in double poly greenhouse with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: Unreleased proprietary hybrid *Heuchera* 12-62-03 as the female (seed parent); unreleased proprietary hybrid *Tiarella* 11-14-08 as the male (pollen); parentage of the female comprises *Heuchera* 'Fire Chief' U.S. Plant Pat. No. 21,880, *Heuchera* 'Mocha Mint' (not patented) and *Heuchera* 'Milan' U.S. Plant Pat. No. 21,682; lineage of the male parent comprises *Tiarella* 'Pink Brushes' U.S. Plant Pat. No. 13,329 and *Tiarella* 'Cascade Creeper' U.S. Plant Pat. No. 21,925;

Plant habit: Hardy herbaceous perennial of tightly compact rhizomes with basal rosette of mounded foliage; foliage of two-year-old plant about 18 cm tall and 46 cm in diameter, foliage of three-year-old plant about 26 cm tall and 56 cm diameter;

Roots: Fibrous, finely branched; when actively growing near white in color depending on soil type;

Growth rate: Rapid, rooting from cutting in 2 weeks and finishing in three-liter container in about 3 months; beginning to flower in 6 to 8 weeks following a 9 week vernalization;

Foliage: Leaf blade puberulent abaxial and adaxial; palmately five-lobed to seven-lobed, lobes incised typically to less than one third of the way to petiole; matte surface above and below; lobe apices acute to mucronulate; base truncate to cordate with lobes typically not imbricate; blade to about 11.8 cm long and 12.5 cm wide, average about 10.2 cm long and 10.8 cm wide; center lobe to about 5.5 cm long and 3.8 cm wide at base, average about 5.0 cm long and 3.5 cm wide;

Foliage color: Leaf color is seasonally variable; young expanding leaves adaxial apices nearest RHS 146D, region in mid-portion nearest RHS 160A, surrounding veins between RHS 187C and RHS 60A; young expanding abaxial leaf apices nearest RHS N144D, region in mid-portion RHS 160C blushed with RHS 187C, surrounding veins nearest RHS 187B; flowering and mid-season adaxial mid-portion nearest RHS 146D with slight silver overlay, surrounding veins nearest RHS 187A with slight silver overlay, and margin 0.5 mm with tinting of nearest RHS 187B; flowering and mid-season abaxial 0.5 mm margin with tinting of nearest RHS 187B, mid-portion between RHS 145A and RHS N144D, surrounding veins nearest RHS 187A with overlay of nearest RHS 188B; late fall adaxial mid-portion between RHS 138A and RHS 138B with slight silver overlay, surrounding veins nearest blend of RHS N187A and RHS N189A;

Leaf margin: Ciliolate; serrulate;

Leaf apex: Acute;

Leaf base: Cordate; lobes seldom imbricate;

Leaf surface: Puberulent to pubescent adaxial and abaxial;

Leaf quantity: Dense, about six per division and 260 per three-year-old plant;

Veins: Palmate, pubescent adaxial and abaxial;

Vein color: Adaxial expanding foliage between RHS 170D and RHS N170D and abaxial nearest RHS 160D; mid-season and flowering adaxial main and secondary veins nearest RHS N144D, mid-season and flowering abaxial main veins nearest RHS 160D;

Petiole: Terete; pubescent; base clasping; to 20.5 cm long and 4.0 mm diameter base; average about 16.5 cm long and 3.5 mm diameter at base; wiry but flexible;

Petiole color: On emerging foliage distally nearest RHS 150D and in basal one-half with light blush nearest RHS 182C with RHS 150 undertone; mid-season and flowering between RHS 187C and RHS 160D with increased tinting of RHS 187C with more intense light;

Inflorescence: In lightly branched panicle, about thirty racemes per plant; about 90 flowers per panicle; first panicle flowering beginning in late spring with repeat racemes flowering into summer; individual panicles remaining in flower for about four weeks; flower attitude mostly outwards; individual flowers remaining effective for about 4 days;

Fragrance: None detected;

Peduncle: Terete, erect; glandular, puberulent to pubescent; to about 48.0 cm tall and 3.5 mm diameter at base, average about 32.0 cm tall and 3.3 mm diameter base; flowering portion about 13.0 cm long and 5.5 cm across;

Peduncle attitude: Upright; erect;

Peduncle branches: In lower three-quarters of flowering portion of peduncle with average of 3.5 flowers per branch on 20 branches; branches to about 9.0 cm long and about 0.8 mm diameter at base;

Peduncle color: Distal region between RHS 183C and RHS N186C and basal region nearest RHS183C;

Pedicel: Terete; puberulent to glandular; to about 4.0 mm long and 0.5 mm in diameter, average about 3.5 mm long and 0.5 mm diameter at base;

Pedicel color: Proximally nearest RHS 187B, distally nearest RHS 186B;

Buds one day prior to opening: Ellipsoid with rounded apex, and attenuate base; about 3.5 mm long and 2.0 mm diameter;

Bud color: Nearest RHS 60D;

Flower: Perfect, campanulate, actinomorphic; about 6.0 mm deep and 8.0 mm in diameter at face; individual flowers lasting about three to four days on plant or as cut raceme;

Calyx: Campanulate; five sepals; glandular abaxial, glabrous adaxial; apex acute, fused in basal 3.0 mm into hypanthium; margin entire; sepals about 5.5 mm long and 1.5 mm wide at point of fusion;

Calyx color: Abaxial base nearest RHS 63B, abaxial distal portion nearest RHS 64D; adaxial near white nearest RHS 63C;

Petals: Five; adnate to calyx; spatulate, acute apex, narrow attenuate base; margin entire; finely puberulent outside and glabrous inside; about 4.0 mm long and 1.0 mm wide;

Petal color: Abaxial and adaxial nearest RHS NN155D;

Androecium:

*Filaments*.—Five, thin, about 4.0 mm long and less than 0.5 mm in diameter; color white, lighter than RHS N155D.

*Anthers*.—Basifixed; oblong to about 0.5 mm long and about 0.2 mm wide; color nearest RHS N25A.

*Pollen*.—Not observed under present conditions.

Gynoecium:

*Pistil*.—One central two-beaked pistil.

*Style*.—About 6.0 mm long and 0.2 mm at apex flaring to 2.0 mm at base; color nearest RHS 155A.

*Stigma*.—Minute, about 0.2 mm diameter; color nearest RHS 155D.

*Ovary*.—Two carpels; ovoid, apex tapering to meet style; rounded base and sides; about 2.0 mm across at base and 2.5 mm tall; color nearest RHS 155A.

Fruit and seed: Not observed;

Disease and pest tolerance: X *Heucherella* 'Eye Spy' grows best with ample moisture and good drainage in part shade or protection from sum in the hottest part of the day. Cold hardy from USDA zones 4 to 9. X *Heucherella* 'Eye Spy' is able to tolerate heat and humidity better than many X *Heucherella*. Other pest and disease resistance and tolerance outside of that normal for X *Heucherella* is not known.

It is claimed:

1. The new and distinct ornamental plant named X *Heucherella* 'Eye Spy' as herein described and illustrated.

* * * * *